US005748389A

United States Patent [19]
Gering et al.

[11] Patent Number: 5,748,389
[45] Date of Patent: May 5, 1998

[54] OPTICAL PEDESTAL AND METHOD FOR USING THE SAME

[75] Inventors: Marcus J. Gering, Mesa; Gordon O. Berg; David C. Lehnen, both of Tempe; Joseph W. Frisbie, Mesa, all of Ariz.

[73] Assignee: Motorola, Inc., Schaumburg, Ill.

[21] Appl. No.: 723,819

[22] Filed: Sep. 30, 1996

[51] Int. Cl.$^6$ .................................................. G02B 7/02
[52] U.S. Cl. .................. 359/811; 359/385; 359/475; 359/599; 359/894; 362/30; 362/31; 356/71
[58] Field of Search .......................... 359/811, 800, 359/819, 894, 397, 398, 385, 475, 707, 599; 362/28, 29, 30, 31; 356/71

[56] References Cited

U.S. PATENT DOCUMENTS

| | | | |
|---|---|---|---|
| 5,142,274 | 8/1992 | Murphy et al. | 362/30 |
| 5,165,772 | 11/1992 | Wu | 362/31 |
| 5,404,277 | 4/1995 | Lindblad | 362/31 |
| 5,485,318 | 1/1996 | Lebby et al. | 359/811 |
| 5,546,888 | 8/1996 | Skiver et al. | 362/31 |
| 5,550,715 | 8/1996 | Hawkins | 362/31 |
| 5,596,402 | 1/1997 | Markantes et al. | 356/71 |
| 5,617,251 | 4/1997 | Ohta et al. | 359/599 |

*Primary Examiner*—Loha Ben
*Attorney, Agent, or Firm*—Rennie William Dover; Ziye Zhou

[57] ABSTRACT

An optical housing (30) includes an optical pedestal (10), a light-blocking mask (31), and a translucent light diffuser (32). The optical housing (30) is used to inspect a work piece (51) placed on a top surface (21) of the optical pedestal (10). Diffusive light is transmitted from the translucent light diffuser (32) into the optical pedestal (10) via a portion of an optically polished bottom surface (11) that is uncovered by the light-blocking mask (31). In the optical pedestal (10), light is reflected by an optically polished inclined surface (23) and refracted by another optically polished inclined surface (25). When light is transmitted away from the optical pedestal (10) after being refracted, it is a collinear light beam and substantially parallel to the top surface (21) of the optical pedestal (10).

20 Claims, 4 Drawing Sheets

OPTICAL PEDESTAL AND METHOD FOR USING THE SAME

BACKGROUND OF THE INVENTION

The present invention relates, in general, to inspecting work pieces and, more particularly, to providing light for inspecting the work pieces.

Typically, work pieces such as semiconductor devices are visually inspected to insure that they meet design specifications for parameters such as lead coplanarity, lead length, lead straightness, mark inspection, surface inspection, lead pitch, etc. A common approach for performing the inspection includes using a machine vision system. Two common techniques for providing light in machine vision systems are front lighting and back lighting techniques.

In the front lighting technique, light is transmitted to the leads of a work piece such as a semiconductor device and is reflected off the lead into a camera. The signal from the camera is then processed by a vision computer to determine whether the work piece meets the desired specifications. A limitation of this system is that metal leads are reflective and can cast hot spots, cold spots, or other distortions to the camera, which lead to inaccurate results being generated by the vision computer.

In the back lighting technique, a silhouette of the leads is generated by a light source positioned behind the leads. The silhouette is received by a camera and processed by a vision computer. More particularly, the light is generated from light emitting diodes embedded in a translucent white plastic light diffuser. The plastic light diffuser also serves as a fixture to support, the semiconductor device being inspected. Because the light is scattered in all directions as it leaves the plastic light diffuser, some of the light hits the front part of the leads, which results in a reduction in the contrast between the back light and silhouette. A reduced contrast may cause erroneous measurements, which leads to the acceptance of bad parts or the rejection of good parts. Further, the plastic is susceptible to wear from the metal leads.

Accordingly, it would be advantageous to have a method and a structure for providing substantially collinear light to an inspection system. It would be desirable for the method to provide collinear light to the back of the leads and for the structure to provide mechanical hardness for preventing abrasion and wear.

DETAILED DESCRIPTION OF THE DRAWINGS

Figure 1:
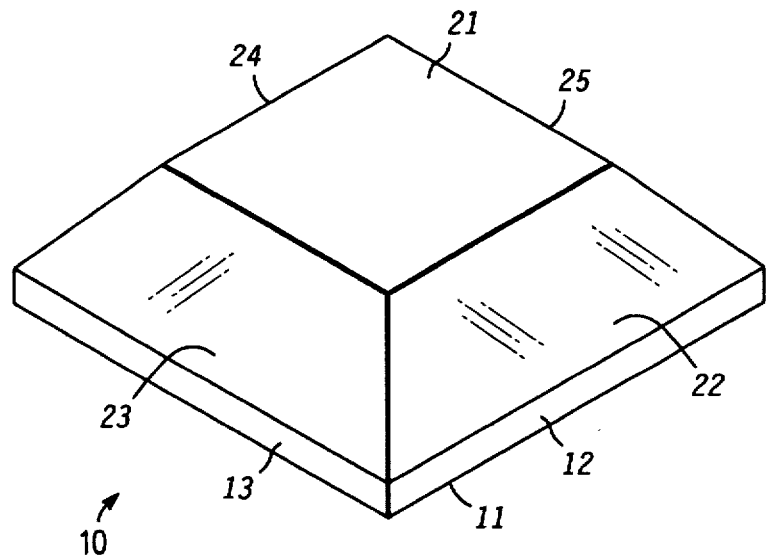
FIG. 1 is an isometric view of an optical pedestal in accordance with a first embodiment of the present invention.

FIG. 1 is an isometric view of an optical pedestal 10 in accordance with a first embodiment of the present invention. Optical pedestal 10 is a modified truncated tetrahedral pyramid having five optically polished surfaces and five unpolished surfaces. More particularly, optical pedestal 10 has a base or bottom surface 11 that is optically polished and four unpolished surfaces that are perpendicular to bottom surface 11. The four unpolished surfaces perpendicular to bottom surface 11 are commonly referred to as girdles or sides. It should be noted that only two girdles 12 and 13 are shown in FIG. 1. Four optically polished inclined surfaces extend from corresponding girdles. For example, an optically inclined surface 22 extends from girdle 12 and an optically inclined surface 23 extends from girdle 13. Optical pedestal 10 further includes an unpolished top surface 21 which is parallel to bottom surface 11 and intersects optically polished inclined surfaces 22, 23, 24 and 25. The girdles are optional features that prevent chipping to optical pedestal 10 and provide additional support.

Suitable materials for optical pedestal 10 include synthetic corundum, cubic zirconia, diamond, or the like. Preferably, the material of optical pedestal 10 is optically clear to light in the frequency range being used, such as visible light, infrared radiation, ultraviolet radiation, etc. The material of optical pedestal 10 also preferably has a high refractive index and a high mechanical hardness. Optically transparent materials having a refractive index greater than 1.65 and a mechanical hardness greater than 7.5 on Mohs' scale are suitable for optical pedestal 10. In a preferred embodiment, optical pedestal 10 is made of an optically transparent material having a refractive index of at least 1.7 and a mechanical hardness of at least 8 on Mohs' scale.

Figure 2:
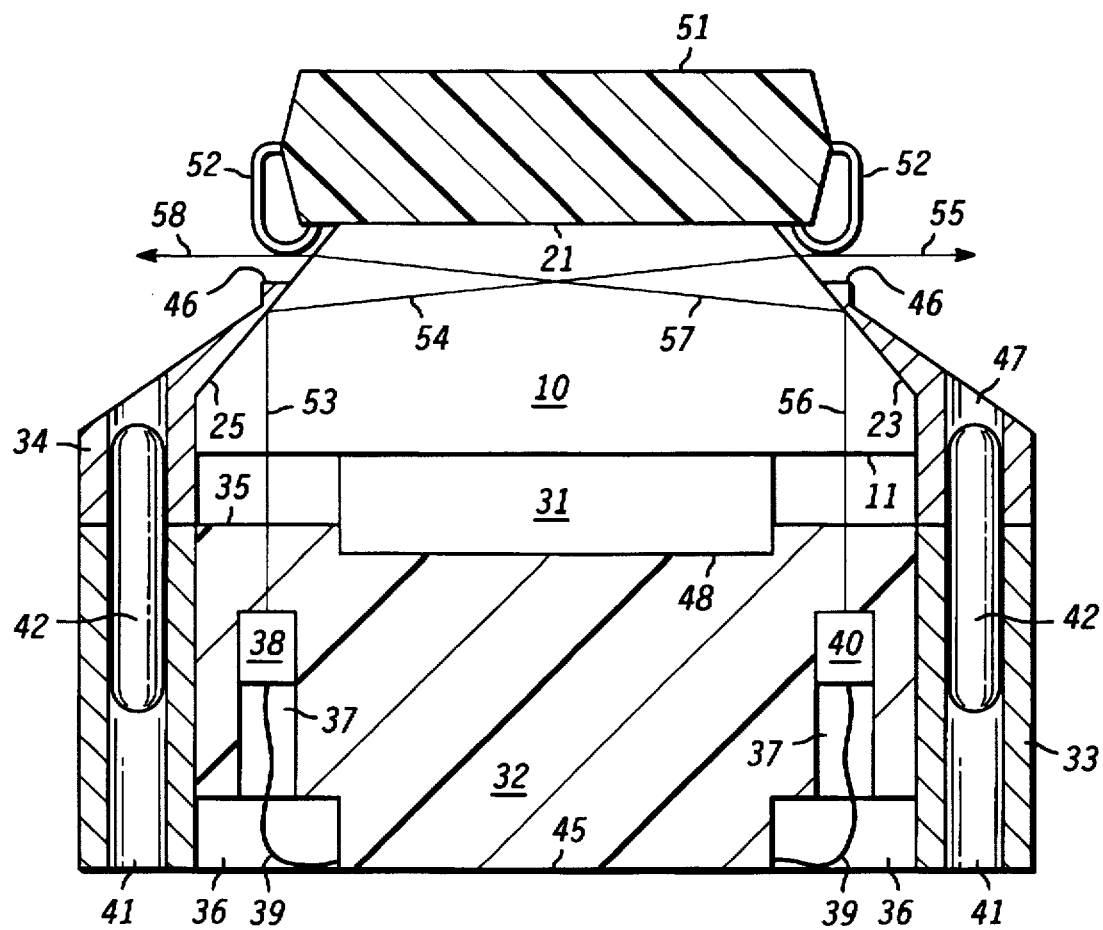
FIG. 2 is a cross-sectional view of an optical housing including the optical pedestal of FIG. 1.

FIG. 2 is a cross-sectional view of an optical housing 30 that includes optical pedestal 10, a light-blocking mask 31, a translucent light diffuser 32, a lower housing 33, and an upper housing 34. By way of example, lower and upper housings 33 and 34, respectively, are metallic. Translucent light diffuser 32 is comprised of a white diffusing translucent material such as, for example, an acetal plastic material sold under the trademark DELRIN.

A notch 48 is formed in a surface 35 of translucent light diffuser 32 for receiving light-blocking mask 31. Light-blocking mask 31 partially blocks the light transmitted to optical pedestal 10. Translucent light diffuser 32 includes an annular shaped notch 36 adjacent a surface 45 of translucent light diffuser 32, wherein surface 45 is opposite to surface 35. Translucent light diffuser 32 further includes a plurality of retaining holes 37 which are adapted to receive light sources such as, for example, light emitting diodes (LEDs) 38 and 40. Notch 36 serves as means for wiring the LEDs together. In accordance with an example of the first embodiment, retaining holes 37 do not extend completely through translucent light diffuser 32. The distance between retaining holes 37 and surface 35 may be adjusted to modulate the amount of light that is transmitted through translucent light diffuser 32 to optical pedestal 10. To increase the amount of the diffusive light transmitted through translucent light diffuser 32 to optical pedestal 10, the distance between surface 35 and retaining holes 37 should be decreased. Collectively, optical pedestal 10, light-blocking mask 31, translucent light diffuser 32, and LEDs 38 and 40 form an optical nest or a back light generating assembly.

Lower housing 33 is aligned to upper housing 34 by aligning pin holes 41 in lower housing 33 to the corresponding pin holes 47 in upper housing 34 and inserting an alignment pin 42 into each pin hole 41. Then, screws (not shown) are screwed into the screw holes (not shown) to fasten lower housing 33 to upper housing 34, thereby forming a housing assembly. By way of example, upper housing 34 is pyramidally shaped and has four external sidewalls. Each sidewall has an optical reference 46, which is precisely ground flat and serves as a known reference. An inner portion of upper housing 34 is shaped to receive optical pedestal 10.

In operation, the light sources such as LEDs 38 and 40 are powered via signal lines 39. The light emitted by LED 38 is transmitted through translucent light diffuser 32 to optical pedestal 10 along a light path 53. The light is reflected from inclined surface 25 of optical pedestal 10 and is then transmitted along a light path 54. The light transmitted along light path 54 is refracted by inclined surface 23 and is then transmitted away from optical pedestal 10 along a light path 55. The light leaving optical pedestal 10 along light path 55 is substantially parallel to top surface 21 of optical pedestal 10. Likewise, the light emitted by LED 40 is transmitted through translucent light diffuser 32 to optical pedestal 10 along a light path 56. The light is reflected from inclined surface 23 of optical pedestal 10 and is then transmitted along a light path 57. The light transmitted along light path 57 is refracted by inclined surface 25 and is then transmitted away from optical pedestal 10 along a light path 58. The light leaving optical pedestal 10 along light path 58 is substantially parallel to top surface 21 of optical pedestal 10.

In the example described herein, there are eight LEDs positioned within translucent light diffuser 32. Two LEDs are positioned along each side of optical pedestal 10. Because FIG. 2 illustrates optical housing 30 in a cross-sectional view, only two sides, i.e., the two sides which include inclined surfaces 23 and 25, and only two LEDs, i.e., LEDs 38 and 40, are shown. The light emitted from these LEDs travels through optical pedestal 10 in a fashion similar to that described for the light emitted from LEDs 38 and 40. After the light travels along light path 55 or 58, it is collected by one or more cameras and transmitted to a vision computer for processing.

Optical housing 30 is used to inspect a workpiece such as, for example, a semiconductor device 51, placed on top surface 21 of optical pedestal 10. Therefore, optical housing 30 is also referred to as a vision lead inspection station. Semiconductor device 51 has a plurality of J-leads 52. Typically, each lead is of slightly different length from other leads. Optical housing 30 can be used to measure the coplanarity of the leads of semiconductor device 51. This is achieved by measuring the height of each lead from respective optical reference 46 of optical housing 30. If the leads in a semiconductor device do not satisfy a coplanarity design specification, the device is rejected.

Figure 3:
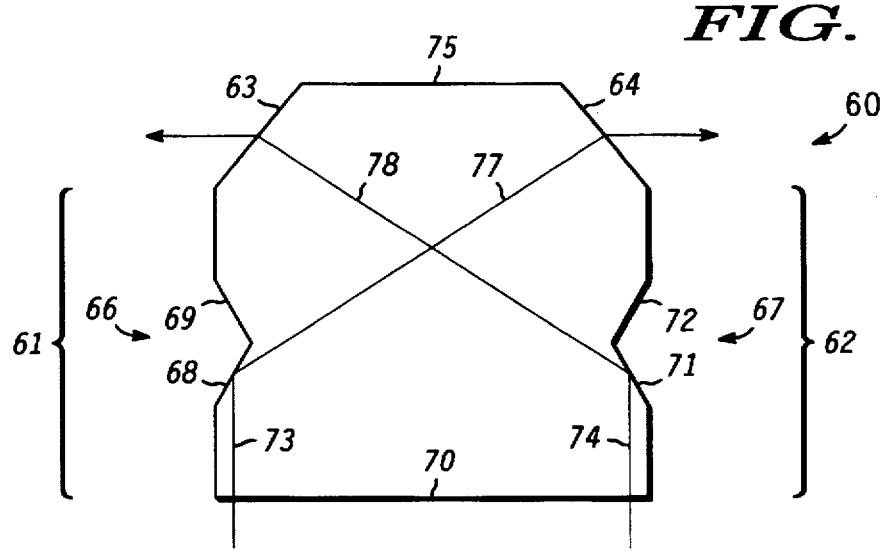
FIG. 3 is a cross-sectional view of an optical pedestal in accordance with a second embodiment of the present invention.

FIG. 3 is a cross-sectional view of an optical pedestal 60 in accordance with a second embodiment of the present invention. Optical pedestal 60 is made of an optically transparent material having similar optical and mechanical properties as that of optical pedestal 10 of FIG. 1. Optical pedestal 60 has four sides and bottom surface 70 and top surface 75. The four sides are also referred to as coupling surfaces which couple top surface 75 to bottom surface 70. Because FIG. 3 shows optical pedestal 60 in a cross-sectional view, only two of the four sides are shown, i.e., sides 61 and 62. Each side further includes an optically polished inclined surface and a notch. Only two of the four optically polished inclined surfaces and only two of the four notches are shown, i.e., optically polished inclined surfaces 63 and 64 and notches 66 and 67. Each of the notches includes an optically polished sidewall surface and an unpolished surface. For example, notch 66 includes an optically polished sidewall surface 68 and an unpolished surface 69, and notch 67 includes an optically polished sidewall surface 71 and an unpolished surface 72. Bottom surface 70 of optical pedestal 60 is also an optically polished surface. Accordingly, optical pedestal 60 has nine optical surfaces. Like optically polished inclined surface 63 and 64, optically polished sidewall surfaces 68 and 71 are preferably flat. FIG. 3 also shows that sidewall surfaces 68 and 71 are substantially parallel to optically polished inclined surfaces 63 and 64, respectively. However, this is not intended as a limitation of the present invention.

Optical pedestal 60 performs the same function as optical pedestal 10 of FIG. 1 and cooperates with an optical housing similar to optical housing 30 shown in FIG. 2. In operation, light is transmitted through bottom surface 70 to optically polished sidewall surfaces 68 and 71 along light transmission paths 73 and 74, respectively. The light is reflected from optically polished sidewall surfaces 68 and 71 to optically polished inclined surfaces 64 and 63, respectively, along the respective light paths 77 and 78. The light travels through optically polished inclined surfaces 64 and 63 and is refracted such that it is substantially parallel to top surface 75 of optical pedestal 60. Because the four optically polished sidewall surfaces, such as sidewall surfaces 68 and 71, reflect light transmitted to optical pedestal 60 from bottom surface 70, they are also referred to as reflective surfaces. Likewise, because the four optically polished inclined surfaces, such as surfaces 63 and 64, refract light transmitted from optically polished sidewall surfaces, they are also referred to as refractive surfaces.

Figure 4:
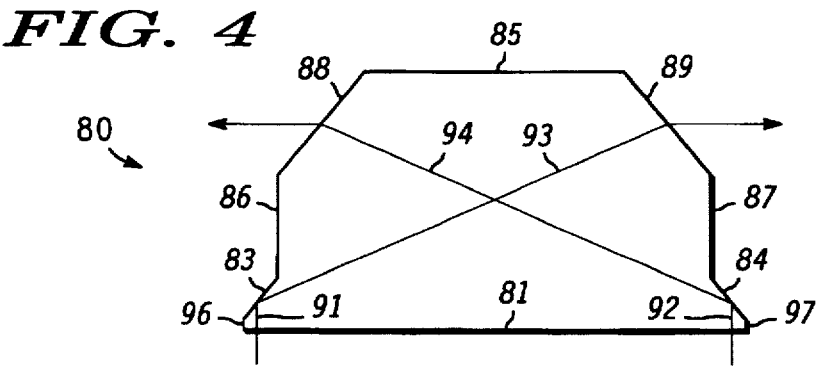
FIG. 4 is a cross-sectional view of an optical pedestal in accordance with a third embodiment of the present invention.

FIG. 4 is a cross-sectional view of an optical pedestal 80 in accordance with a third embodiment of the present invention. Optical pedestal 80 is made of an optically transparent material having similar optical and mechanical properties as that of optical pedestal 10 of FIG. 1. Optical pedestal 80 has nine optical surfaces. More particularly, optical pedestal 80 has an optically polished bottom surface 81 with four unpolished sides extending substantially perpendicularly therefrom. Because FIG. 4 shows optical pedestal 80 in a cross-sectional view, only two of the four unpolished sides are shown, i.e., unpolished sides 96 and 97. Four optically polished reflective surfaces extend from the four unpolished sides. Only two of the four optically polished reflective surfaces are shown in FIG. 4, i.e., reflective surfaces 83 extending from side 96 and reflective surface 84 extending from side 97. Optical pedestal 80 further includes four unpolished surfaces extending from the four reflective surfaces, wherein the four unpolished surfaces are substantially perpendicular to bottom surface 81. Only two of the four unpolished surfaces are shown in FIG. 4, i.e., surfaces 86 and 87. Four optically polished inclined surfaces extend from the four unpolished surfaces of optical pedestal 80. The four optically polished inclined surfaces and a top surface 85 of optical pedestal 80 form a truncated tetrahedral pyramid. Only two of the four optically polished inclined surfaces are shown, i.e., inclined surfaces 88 and 89. Top surface 85 is substantially parallel to bottom surface 81 of optical pedestal 80. Like optically polished inclined surface 88 and 89, optically polished reflective surfaces 83 and 84 are preferably flat. FIG. 4 also shows that reflective surfaces 83 and 84 are substantially parallel to optically polished inclined surfaces 88 and 89, respectively. However, this is not intended as a limitation of the present invention. It should be understood that the unpolished sides, such as sides 96 and 97, are optional features of optical pedestal 80 that prevent chipping to optical pedestal 80 and provide additional support.

Optical pedestal 80 performs the same function as optical pedestal 10 of FIG. 1 and cooperates with an optical housing similar to optical housing 30 shown in FIG. 2. In operation, light is transmitted through bottom surface 81 to optically polished reflective surfaces 83 and 84 along light transmission paths 91 and 92, respectively. The light is reflected from optically polished reflective surfaces 83 and 84 to optically polished inclined surfaces 89 and 88, respectively, along the respective light paths 93 and 94. The light travels through optically polished inclined surfaces 89 and 88 and is refracted such that it is substantially parallel to top surface 85 of optical pedestal 80. Because the four optically polished inclined surfaces, such as surfaces 88 and 89, refract light transmitted from optically polished reflective surfaces, they are also referred to as refractive surfaces.

Figure 5:
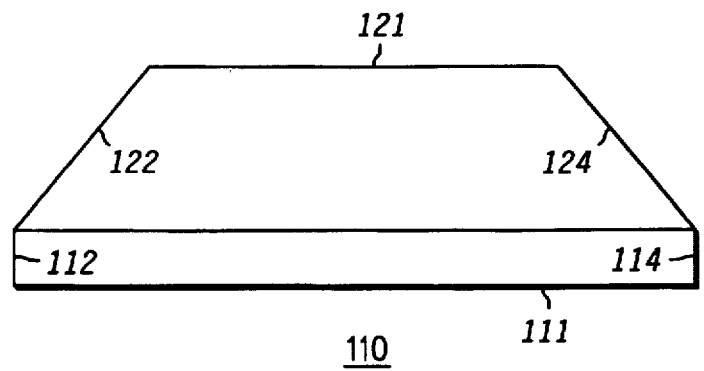
FIG. 5 is a cross-sectional view of an optical pedestal in accordance with a fourth embodiment of the present invention.

FIG. 5 is a cross-sectional view of an optical pedestal 110 in accordance with a fourth embodiment of the present invention. Optical pedestal 110 is made of an optically transparent material having similar optical and mechanical properties as that of optical pedestal 10 of FIG. 1. Optical pedestal 110 is a modified truncated tetrahedral pyramid having eight optically polished surfaces and two unpolished surfaces. More particularly, optical pedestal 110 has a base or bottom surface 111 and a top surface 121 that are unpolished. Four of eight optically polished surfaces are substantially perpendicular to bottom surface 111 and are also referred to as optically polished refractive surfaces. It should be noted that only two refractive surfaces 112 and 114 are shown in FIG. 5. The other four optically polished surfaces extend from refractive surfaces and are also referred to as optically polished inclined surfaces. For example, an optically inclined surface 122 extends from refractive surface 112 and an optically inclined surface 124 extends from refractive surface 114.

Figure 6:
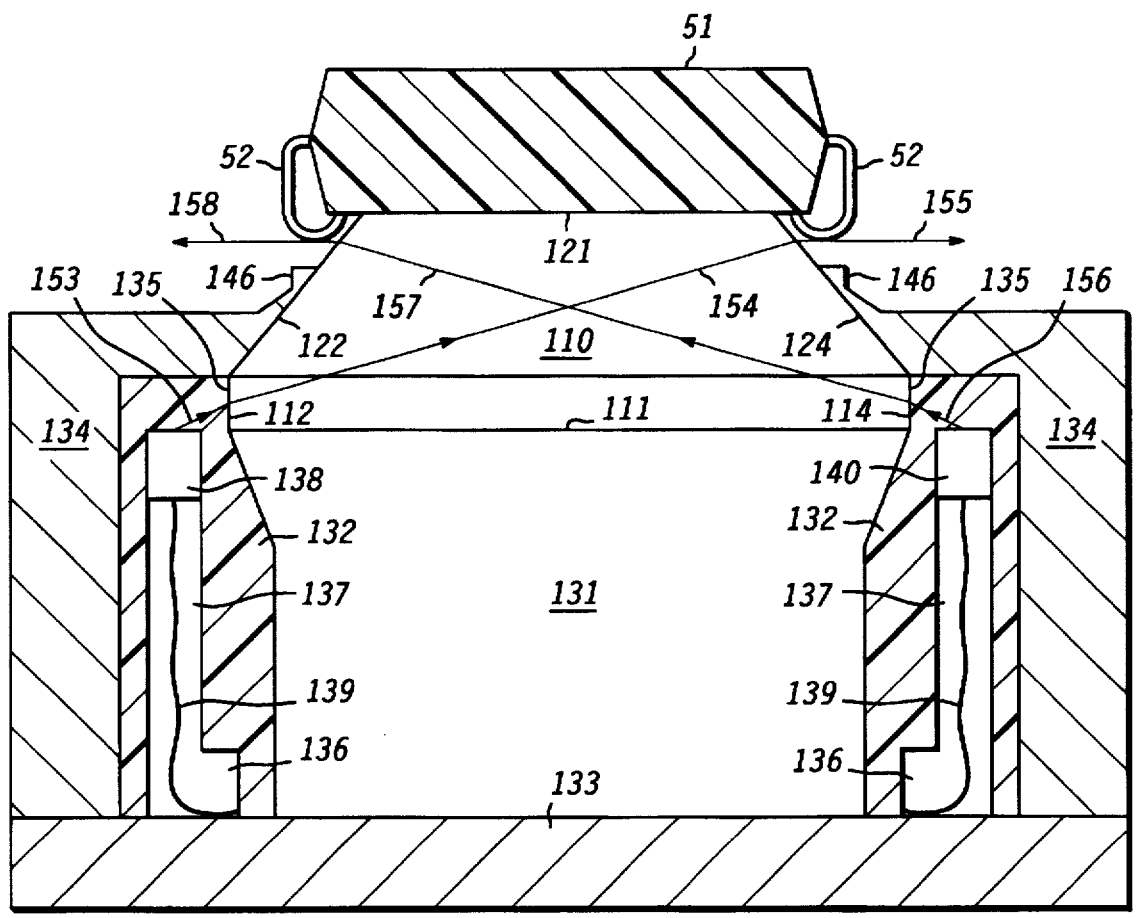
FIG. 6 is a cross-sectional view of an optical housing including the optical pedestal of FIG. 5.

FIG. 6 is a cross-sectional view of an optical housing 130 that includes optical pedestal 110, a light-blocking mask 131, a translucent light diffuser 132, a lower housing 133, and an upper housing 134. It should be noted that the same reference numbers are used in the figures to represent the same elements. By way of example, lower and upper housings 133 and 134, respectively, are metallic. Translucent light diffuser 132 is comprised of a white diffusing translucent material such as, for example, an acetal plastic material sold under the trademark DELRIN.

Light-blocking mask 131 completely blocks the light transmitted to optical pedestal 110 through bottom surface 111. Translucent light diffuser 132 includes an annular shaped notch 136. Translucent light diffuser 132 further includes a plurality of retaining holes 137 which are adapted to receive light sources such as, for example, light emitting diodes (LEDs) 138 and 140. Notch 136 serves as means for wiring the LEDs together. In accordance with an example of the fourth embodiment, retaining holes 137 do not extend completely through translucent light diffuser 132. The distance between retaining holes 137 and a surface 135 adjacent the refractive surfaces, such as refractive surfaces 112 and 114, may be adjusted to modulate the amount of light that is transmitted through translucent light diffuser 132 to optical pedestal 110. To increase the amount of the diffusive light transmitted through translucent light diffuser 132 to optical pedestal 110, the distance between surface 135 and retaining holes 137 should be decreased. Collectively, optical pedestal 110, light-blocking mask 131, translucent light diffuser 132, and LEDs 138 and 140 form an optical nest or a back light generating assembly.

Lower housing 133 is aligned to upper housing 134 by aligning pin holes (not shown) in lower housing 133 to the corresponding pin holes (not shown) in upper housing 134 and inserting an alignment pin (not shown) into each pin hole. Then, screws (not shown) are screwed into the screw holes (not shown) to fasten lower housing 133 to upper housing 134, thereby forming a housing assembly. By way of example, upper housing 134 has four external sidewalls. Each sidewall has an optical reference 146, which is precisely ground flat and serves as a known reference. An inner portion of upper housing 134 is shaped to cooperate with light-blocking mask 131 and translucent light diffuser 132 for receiving optical pedestal 110.

In operation, the light sources such as LEDs 138 and 140 are powered via signal lines 139. The light emitted by LED 138 is transmitted through translucent light diffuser 132 to optical pedestal 110 along a light path 153. The light is refracted by refractive surface 112 of optical pedestal 110 and is then transmitted along a light path 154. The light transmitted along light path 154 is refracted by inclined surface 124 and is then transmitted away from optical pedestal 110 along a light path 155. The light leaving optical pedestal 110 along light path 155 is substantially parallel to top surface 121 of optical pedestal 110. Likewise, the light emitted by LED 140 is transmitted through translucent light diffuser 132 to optical pedestal 110 along a light path 156. The light is refracted by refractive surface 114 of optical pedestal 110 and is then transmitted along a light path 157. The light transmitted along light path 157 is refracted by inclined surface 122 and is then transmitted away from optical pedestal 110 along a light path 158. The light leaving optical pedestal 110 along light path 158 is substantially parallel to top surface 121 of optical pedestal 110.

In the example described herein, there are eight LEDs positioned within translucent light diffuser 132. Two LEDs are positioned along each side of optical pedestal 110. Because FIG. 6 illustrates optical housing 130 in a cross-sectional view, only two sides, i.e., the two sides which include inclined surfaces 122 and 124, and only two LEDs, i.e., LEDs 138 and 140, are shown. The light emitted from these LEDs travels through optical pedestal 110 in a fashion similar to that described for the light emitted from LEDs 138 and 140. After the light travels along light path 155 or 158, it is collected by one or more cameras and transmitted to a vision computer for processing.

Optical housing 130 is used to inspect a work piece such as, for example, a semiconductor device 51, placed on top surface 121 of optical pedestal 110. Therefore, optical housing 130 is also referred to as a vision lead inspection station or a vision inspection station. The procedure of inspecting of semiconductor device 51 placed on optical pedestal 110 is similar to that described with reference to FIG. 2.

Figure 7:
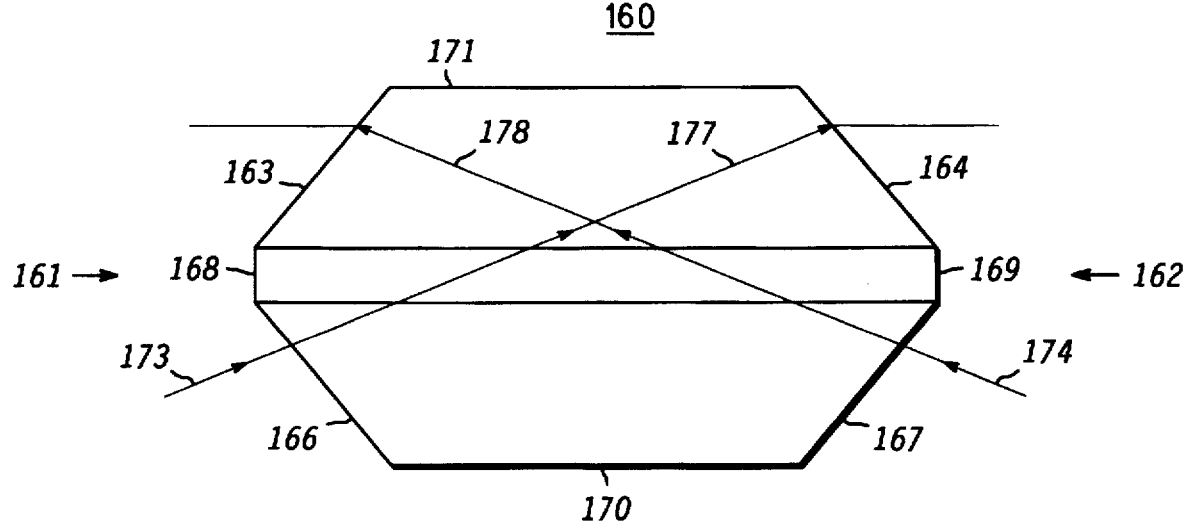
FIG. 7 is a cross-sectional view of an optical pedestal in accordance with a fifth embodiment of the present invention.

FIG. 7 is a cross-sectional view of an optical pedestal 160 in accordance with a fifth embodiment of the present invention. Optical pedestal 160 is made of an optically transparent material having similar optical and mechanical properties as that of optical pedestal 10 of FIG. 1. Optical pedestal 160 has a bottom surface 170, a top surface 171, and four sides or coupling surfaces between bottom surface 170 and top surface 171. Because FIG. 7 shows optical pedestal 160 in a cross-sectional view, only two of the four sides are shown, i.e., sides 161 and 162. Each side further includes an optically polished inclined surface and an optically polished refractive surface. Only two of the four optically polished inclined surfaces, i.e., optically polished inclined surfaces 163 and 164, and two of the four optically polished refractive surfaces, i.e., optically polished refractive surfaces 166 and 167, are shown. The four optically polished inclined surfaces are separated from their respective optically polished refractive surfaces by four unpolished side surfaces. FIG. 7 only shows two unpolished side surfaces, i.e., side surface 168 between inclined surface 163 and refractive surface 166 and side surface 169 between inclined surface 164 and refractive surface 167. Bottom surface 170 and top surface 171 of optical pedestal 160 are unpolished surfaces. Accordingly, optical pedestal 160 has eight optical surfaces and six unpolished surfaces. It should be understood that the unpolished side surfaces, such as side surfaces 168 and 169, are optional features of optical pedestal 160.

Optical pedestal 160 performs the same function as optical pedestal 110 of FIG. 5 and cooperates with an optical housing similar to optical housing 130 shown in FIG. 6. In operation, light is transmitted into optical pedestal 160 through optically polished refractive surfaces 166 and 167 along light transmission paths 173 and 174, respectively. The light is refracted by optically polished refractive surfaces 166 and 167 toward optically polished inclined surfaces 164 and 163, respectively, along the respective light paths 177 and 178. The light travels through optically polished inclined surfaces 164 and 163 and is refracted such that it is substantially parallel to top surface 171 of optical pedestal 160. FIG. 7 shows light paths 173 and 174 being perpendicular to refractive surfaces 166 and 167, respectively. Accordingly, refractive surfaces 166 and 167 do not change the direction of the light propagating along light paths 173 and 174, respectively. Therefore, light path 177 is in the same direction as light path 173, and light path 178 is in the same direction as light path 174. It should be noted that this is not intended as a limitation of the present invention. Alternatively, light paths 173 and 174 are not perpendicular to refractive surfaces 166 and 167, respectively, and light paths 177 and 178 are in different directions from respective light paths 173 and 174.

By now it should be appreciated that a method and a structure for providing substantially collinear or collimated light to an inspection system have been provided. The method and structure of the present invention provide collinear light to back light the work piece being inspected. Furthermore, the optical pedestal of the present invention is resistant to abrasion and wear.

While specific embodiments of the invention have been shown and described, further modifications and improvements will occur to those skilled in the art. It is understood that this invention is not limited to the particular forms shown and it is intended for the appended claims to cover all modifications of the invention which fall within the true spirit and scope of the invention. For example, the translucent light diffuser in the optical housing may be replaced with a collinear light source.

We claim:

1. A method for using an optical pedestal to back light a work piece, comprising the steps of:

placing the work piece adjacent a first surface of the optical pedestal;

transmitting light into the optical pedestal through an optically polished surface of the optical pedestal; and refracting the light through a first optically polished inclined surface away from the optical pedestal, wherein the light refracted by the first optically polished inclined surface is substantially parallel to the first surface of the optical pedestal.

2. The method of claim 1, wherein the step of transmitting light into the optical pedestal through an optically polished surface further includes the steps of:

transmitting the light into the optical pedestal through an optically polished second surface of the optical pedestal, the optically polished second surface being substantially parallel to the first surface of the optical pedestal; and reflecting the light from a second optically polished inclined surface toward the first optically polished inclined surface of the optical pedestal, the second optically polished inclined surface being opposite to the first optically polished inclined surface.

3. The method of claim 2, wherein the step of transmitting light into the optical pedestal further includes the steps of:

partially blocking the optically polished second surface of the optical pedestal with a light-blocking mask; and transmitting a diffusive light into the optical pedestal through the optically polished second surface of the optical pedestal.

4. The method of claim 2, further comprising the steps of:

reflecting the light from the first optically polished inclined surface toward the second optically polished inclined surface of the optical pedestal; and refracting the light through the second optically polished inclined surface away from the optical pedestal, wherein the light refracted by the second optically polished inclined surface is substantially parallel to the first surface of the optical pedestal.

5. The method of claim 1, wherein the step of transmitting light into the optical pedestal through an optically polished surface further includes the steps of:

blocking a second surface of the optical pedestal with a light-blocking mask, the second surface being substantially parallel to the first surface; and transmitting the light into the optical pedestal by refracting the light through a first optically polished refractive surface toward the first optically polished inclined surface of the optical pedestal.

6. The method of claim 5, further including the steps of:

transmitting the light into the optical pedestal by refracting the light through a second optically polished refractive surface toward a second optically polished inclined surface of the optical pedestal; and refracting the light through the second optically polished inclined surface away from the optical pedestal, wherein the light refracted by the second optically polished inclined surface is substantially parallel to the first surface of the optical pedestal.

7. An optical pedestal, comprising:

an unpolished first surface;

a second surface substantially parallel to the unpolished first surface;

a first optically polished inclined surface between the unpolished first surface and the second surface; and a second optically polished inclined surface between the unpolished first surface and the second surface and opposite to the first optically polished inclined surface.

8. The optical pedestal of claim 7, wherein the optical pedestal is made of an optically transparent material having a refractive index higher than approximately 1.65 and a mechanical hardness higher than approximately 7.5 on Mohs' scale.

9. The optical pedestal of claim 7, wherein the second surface is optically polished.

10. The optical pedestal of claim 9, further comprising:

a first coupling surface between the first optically polished inclined surface and the second surface and substantially perpendicular to the second surface; and a second coupling surface between the second optically polished inclined surface and the second surface and substantially perpendicular to the second surface.

11. The optical pedestal of claim 10, wherein:

the first coupling surface has a first notch substantially parallel to the second surface, the first notch including a first optically polished sidewall surface; and the second coupling surface has a second notch substantially parallel to the second surface, the second notch including a second optically polished sidewall surface.

12. The optical pedestal of claim 10, further comprising:

a first optically polished reflective surface between the first coupling surface and the second surface; and a second optically polished reflective surface between the second coupling surface and the second surface.

13. The optical pedestal of claim 7, wherein the second surface is unpolished.

14. The optical pedestal of claim 13, further comprising:

a first optically polished refractive surface between the first optically polished inclined surface and the second surface; and a second optically polished refractive surface between the second optically polished inclined surface and the second surface.

15. The optical pedestal of claim 14, further comprising:

a first coupling surface between the first optically polished inclined surface and the first optically polished refractive surface, the first coupling surface being substantially perpendicular to the second surface; and a second coupling surface between the second optically polished inclined surface and the second optically polished refractive surface, the second coupling surface being substantially perpendicular to the second surface.

16. A vision inspection station, comprising: an optical pedestal, which comprises:

a first surface for receiving a work piece;

a second surface substantially parallel to the first surface;

a first optically polished inclined surface between the first surface and the second surface; and a second optically polished inclined surface between the first surface and the second surface and opposite to the first optically polished inclined surface;

a light-blocking mask adjacent the second surface of the optical pedestal, the light-blocking mask blocking, at least partially, a transmission of light into the optical pedestal through the second surface;

a translucent light diffuser adjacent the light-blocking mask; and a light source attached to the translucent light diffuser.

17. The vision inspection station of claim 16, further comprising an optical reference adjacent the first optically polished inclined surface of the optical pedestal.

18. The vision inspection station of claim 16, wherein:

the translucent light diffuser has a retaining hole formed therein; and the light source is located in the retaining hole of the translucent light diffuser.

19. The vision inspection station of claim 16, wherein:

the second surface of the optical pedestal is optically polished;

the translucent light diffuser includes a first surface having a notch formed therein; and the light-blocking mask is in the notch in the first surface of the translucent light diffuser and partially blocks the transmission of light into the optical pedestal through the second surface.

20. The vision inspection station of claim 16, wherein the second surface of the optical pedestal is unpolished and the light-blocking mask completely blocks the transmission of light into the optical pedestal through the second surface.

\* \* \* \* \*